US010709565B2

(12) United States Patent
Humphrey et al.

(10) Patent No.: US 10,709,565 B2
(45) Date of Patent: Jul. 14, 2020

(54) DIRECTIONAL LOCKING REVERSE SHOULDER PROSTHESES AND SYSTEMS

(71) Applicant: Zimmer, Inc., Warsaw, IN (US)

(72) Inventors: Steven Humphrey, Warsaw, IN (US);
James D. Wernle, Warsaw, IN (US);
Joanna Surma, Warsaw, IN (US);
Stephen H. Hoag, Warsaw, IN (US);
Donald W. Dye, Warsaw, IN (US);
Kenton A. Walz, Fort Wayne, IN (US);
Terry W. Wagner, Mishawaka, IN (US); Kathleen Macke, Warsaw, IN (US); Duane Gillard, Pierceton, IN (US); Brian D. Byrd, North Webster, IN (US); Ken Yamaguchi, Chesterfield, MO (US)

(73) Assignee: Zimmer, Inc., Warsaw, IN (US)

(*) Notice: Subject to any disclaimer, the term of this patent is extended or adjusted under 35 U.S.C. 154(b) by 0 days.

(21) Appl. No.: 15/248,868

(22) Filed: Aug. 26, 2016

(65) Prior Publication Data
US 2017/0056187 A1    Mar. 2, 2017

Related U.S. Application Data

(60) Provisional application No. 62/210,600, filed on Aug. 27, 2015.

(51) Int. Cl.
*A61F 2/40* (2006.01)
*A61F 2/30* (2006.01)

(52) U.S. Cl.
CPC .......... *A61F 2/4014* (2013.01); *A61F 2/4081* (2013.01); *A61F 2002/305* (2013.01);
(Continued)

(58) Field of Classification Search
CPC ............................................... A61F 2/40–4081
See application file for complete search history.

(56) References Cited

U.S. PATENT DOCUMENTS 4,784,663 A     11/1988  Kenna
4,938,769 A  *   7/1990  Shaw ..................... A61F 2/389
                                                    623/20.15
(Continued)

FOREIGN PATENT DOCUMENTS

CN     101321507 A    12/2008
CN     104203162 A    12/2014
(Continued)

OTHER PUBLICATIONS

"International Application Serial No. PCT/US2016/049015, International Preliminary Report on Patentability dated Mar. 8, 2018", 8 pgs.
(Continued)

*Primary Examiner* — Marcia L Watkins
(74) *Attorney, Agent, or Firm* — Schwegman Lundberg & Woessner, P.A.

(57) ABSTRACT

The present disclosure relates to prosthesis systems having trays and liners having an asymmetrical locking mechanism to bias the strength of the liner to resist loading forces and associated methods. The tray has a lateral groove disposed in an inner surface of a lateral circumferential portion of the tray and a medial groove disposed in an inner surface of a medial circumferential portion of the tray. The liner has an upper segment and a lower segment. The liner has a locking portion for lockingly engaging the tray that includes the lower segment. The locking portion has a lateral toe positioned generally diametrically opposite a plurality of resiliently deformable medial fingers defined therein. The liner and the tray are engageable in a lateral-to-medial direction so that the plurality of medial fingers can resiliently deform (Continued)

to engage the medial groove subsequent to engagement of the lateral toe within the lateral groove.

12 Claims, 5 Drawing Sheets

(52) U.S. Cl.
CPC .............. *A61F 2002/3054* (2013.01); *A61F 2002/30331* (2013.01); *A61F 2002/30383* (2013.01); *A61F 2002/30522* (2013.01); *A61F 2002/30649* (2013.01); *A61F 2002/4022* (2013.01); *A61F 2002/4037* (2013.01); *A61F 2002/4085* (2013.01)

(56) References Cited

U.S. PATENT DOCUMENTS

| | | | |
|---|---|---|---|
| 4,964,865 A | 10/1990 | Burkhead et al. | |
| 5,935,175 A | 8/1999 | Ostiguy, Jr. et al. | |
| 6,126,692 A | 10/2000 | Robie et al. | |
| 6,569,202 B2 | 5/2003 | Whiteside | |
| 6,679,916 B1 * | 1/2004 | Frankle ................ | A61F 2/4081 623/19.12 |
| 6,869,448 B2 | 3/2005 | Tuke | |
| 6,969,407 B2 | 11/2005 | Klotz et al. | |
| 7,854,768 B2 * | 12/2010 | Wiley ................ | A61F 2/30734 623/19.11 |
| 8,012,215 B2 * | 9/2011 | Metzger ................ | A61F 2/389 623/20.15 |
| 8,062,376 B2 * | 11/2011 | Shultz ................ | A61F 2/40 623/19.11 |
| 8,394,148 B2 | 3/2013 | Otto et al. | |
| 8,500,815 B2 | 8/2013 | Fockens | |
| 8,608,805 B2 * | 12/2013 | Forrer ................ | A61F 2/4014 623/19.12 |
| 8,821,579 B2 | 9/2014 | Jukes et al. | |
| 9,204,967 B2 | 12/2015 | Wyss et al. | |
| 9,283,075 B2 | 3/2016 | Wiley et al. | |
| 9,642,711 B2 | 5/2017 | Carson | |
| 2003/0139817 A1 | 7/2003 | Tuke et al. | |
| 2005/0246027 A1 | 11/2005 | Metzger et al. | |
| 2006/0020344 A1 | 1/2006 | Shultz et al. | |
| 2006/0069445 A1 | 3/2006 | Ondrla et al. | |
| 2007/0173945 A1 | 7/2007 | Wiley et al. | |
| 2008/0228281 A1 | 9/2008 | Forrer et al. | |
| 2009/0076621 A1 * | 3/2009 | Rollet ................ | A61F 2/4014 623/23.45 |
| 2017/0325962 A1 | 11/2017 | Wiley et al. | |

FOREIGN PATENT DOCUMENTS

| | | | |
|---|---|---|---|
| CN | 104755047 A | 7/2015 | |
| CN | 108024858 A | 5/2018 | |
| JP | 2018525160 A | 9/2018 | |
| WO | WO 0001326 A1 * | 1/2000 | ........... A61F 2/4081 |

OTHER PUBLICATIONS

"European Application Serial No. 16760332.3, Response filed Nov. 13, 2018 to Office Action dated May 3, 2018", 13 pgs.
"Chinese Application Serial No. 201680052697.4, Office Action dated Mar. 1, 2019", (W/ English Translation), 23 pgs.
"Chinese Application Serial No. 201680052697.4, Response filed Apr. 4, 2019 to Office Action dated Mar. 1, 2019", (W/ English Claims), 14 pgs.
"Chinese Application Serial No. 201680052697.4, Office Action dated Jul. 19, 2019", (W/ English Translation), 20 pgs.
"Chinese Application Serial No. 201680052697.4, Response filed Sep. 18, 2019 to Office Action dated Jul. 19, 2019", (W/ English Claims), 21 pgs.
"Chinese Application Serial No. 201680052697.4, Decision of Rejection dated Feb. 3, 2020", with English translation, 18 pages.
"Australian Application Serial No. 2016310347, First Examination Report dated Apr. 22, 2020", 4 pages.

* cited by examiner

DIRECTIONAL LOCKING REVERSE SHOULDER PROSTHESES AND SYSTEMS

RELATED APPLICATIONS

This application claims the benefit of priority to U.S. Provisional Patent Application Ser. No. 62/210,600, filed Aug. 27, 2015, the content of which is incorporated herein by reference.

FIELD

The present disclosure relates to prosthesis systems comprising trays and liners, including trays and liners having a locking mechanism.

BACKGROUND

This section provides background information related to the present disclosure, which is not necessarily prior art.

Reverse Shoulder Arthroplasty (RSA) is an alternative to traditional shoulder arthroplasty that is often indicated for use in elderly patients with deficient rotator cuffs. With advancements in RSA designs and simple surgical techniques, the use of RSA has spread to patients that are younger or who do not have rotator cuff deficiency. Traditional reverse shoulder liner locking mechanisms are symmetrical about an axis and therefore have the same strength in any loading orientation, but are limited by a snap lock feature that is deformed during insertion of the articular surface into the humeral stem or tray. The snaps are usually tabs that must be compressed beyond a rigid metal lip or ring.

SUMMARY

This section provides a general summary of the disclosure, and is not a comprehensive disclosure of its full scope or all of its features.

The present inventors have recognized, among other things, that a problem to be solved is that current RSA techniques often times result in the undesirable effects of scapular notching and limited range of motion. Currently practiced solutions to these undesirable effects employ a steeper humeral implant angle and, additionally or alternatively, a lateralized center of rotation. However, a result of these currently practiced solutions is an increased load applied to the liner locking mechanism that can result in liner dissociation. Accordingly, the present teachings provide for systems comprising trays and liners having an asymmetrical locking mechanism to bias the strength of the liner to resist loading forces and associated methods.

In one aspect, a prosthesis system for a joint can comprise a tray and a liner. The tray can have a lateral groove disposed in an inner surface of a lateral circumferential portion of the tray. The tray can also have a medial groove disposed in an inner surface of a medial circumferential portion of the tray. The liner can have an upper segment and a lower segment. At least the lower segment can comprise a locking portion for lockingly engaging the tray. The locking portion can comprise a lateral toe positioned generally diametrically opposite a plurality of resiliently deformable medial fingers defined in the locking portion. The liner and the tray can be engageable in a lateral-to-medial direction so that the plurality of medial fingers can resiliently deform to engage the medial groove subsequent to engagement of the lateral toe within the lateral groove. Upon implantation, the tray and the liner can be selectively rotationally oriented with respect to each other such that the lateral toe of the liner can be engaged within a middle portion of the lateral groove of the tray to resist disassociation of the liner from the tray when the prosthesis is subjected to physiological loading conditions. The medial circumferential portion of the tray can further comprise a medial tab that can extend from an upper surface thereof, and wherein a lower surface of the upper segment of the liner can define a female receptacle for matingly receiving the medial tab of the tray. The lower surface of the upper segment of the liner can define a plurality of female receptacles for receiving the medial tab. Each of the plurality of female receptacles can correspond to a unique angular rotational position between the liner and the tray.

In one aspect, a liner can have an upper segment and a lower segment. At least the lower segment can comprise a locking portion for lockingly engaging a tray. The locking portion can comprise a lateral toe positioned generally diametrically opposite a plurality of resiliently deformable medial fingers defined therein. The tray and the liner can be engageable in a lateral-to-medial direction so that the plurality of medial fingers can resiliently deform to engage a medial groove disposed in an inner surface of a medial circumferential portion of the tray subsequent to engagement of the lateral toe within the lateral groove. Upon implantation, the liner can be selectively rotationally oriented with respect to the tray such that the lateral toe of the liner can be engaged within a middle portion of a lateral groove of the tray to resist disassociation of the liner from the tray when the prosthesis is subjected to physiological loading conditions. The lower surface of the upper segment of the liner can define one or a plurality of female receptacles for matingly receiving a medial tab extending from an upper surface of the medial circumferential portion of the tray. Each of the plurality of female receptacles can correspond to a unique angular rotational position between the liner and the tray.

In another aspect, a tray can have a lateral groove disposed in an inner surface of a lateral circumferential portion of the tray. The tray can also have a medial groove disposed in an inner surface of a medial circumferential portion of the tray. The tray can be engageable with a liner that can have an upper segment and a lower segment. At least the lower segment of the liner can comprise a locking portion for lockingly engaging the tray. The locking portion can comprise a lateral toe positioned generally diametrically opposite a plurality of resiliently deformable medial fingers defined therein. The tray and the liner can be engageable in a lateral-to-medial direction so that the plurality of medial fingers can resiliently deform to engage the medial groove subsequent to engagement of the lateral toe within the lateral groove. Upon implantation, the tray can be selectively rotationally oriented with respect to the liner such that the lateral toe of the liner can be engaged within a middle portion of the lateral groove of the tray to resist disassociation of the liner from the tray when the prosthesis is subjected to physiological loading conditions. The medial circumferential portion of the tray can further comprise a medial tab that can extend from an upper surface thereof for matingly receiving a medial female receptacle defined in the upper segment of the liner. The lateral circumferential portion of the tray can further comprise a lateral tab that can extend from an upper surface thereof for matingly receiving a lateral female receptacle defined in at least a portion of the upper segment of the liner.

In another aspect, the present teachings provide for a method that can comprise the steps of selectively rotationally orienting a tray and a liner with respect to each other such that a lateral toe of a lower segment of a liner can be aligned with a middle portion of a lateral groove disposed in an inner surface of a lateral circumferential portion of the tray; and engaging the lateral toe of the liner in the lateral groove of the tray; engaging a plurality of resiliently deformable medial fingers defined in the lower segment of the liner within a medial groove disposed in an inner surface of a medial circumferential portion of a tray, wherein the medial fingers are disposed generally diametrically opposite the lateral toe; wherein the lateral toe resists disassociation of the liner from the tray when the prosthesis is subjected to physiological loading conditions in use. The method can comprise engaging a medial tab extending from an upper surface of the medial circumferential portion of the tray with a female receptacle defined in the upper segment of the liner. Additionally or alternatively, the method can comprise engaging a lateral tab extending from an upper surface of the lateral circumferential portion of the tray with a lateral female receptacle defined in at least a portion of the upper segment of the liner.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
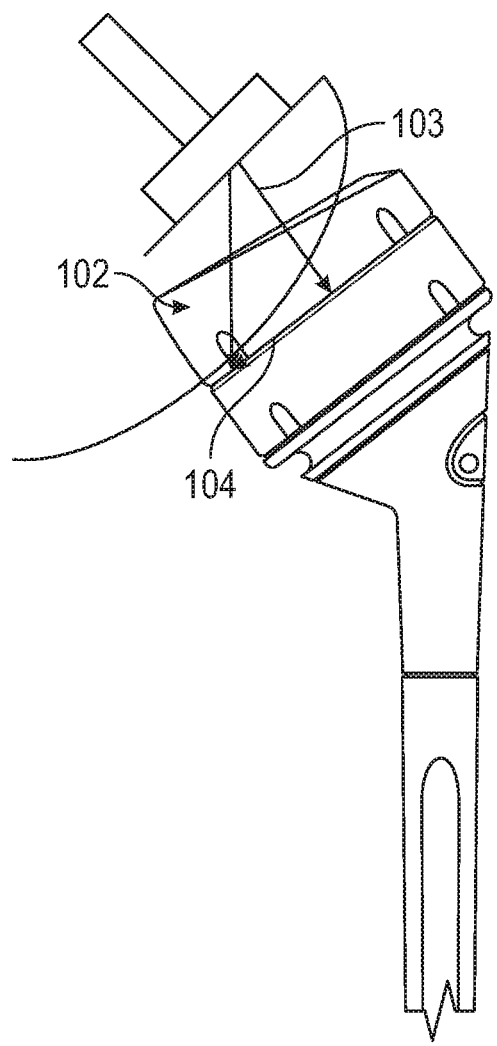
FIG. 1 illustrates exemplary loading conditions of a reverse shoulder arthroplasty prosthesis.

The present teachings provide for systems comprising trays and liners having an asymmetrical locking mechanism to bias the strength of the liner to resist physiological loading forces and associated methods. In a reverse shoulder arthroplasty (RSA) configuration, a metal glenosphere attached to the scapula articulates against a liner attached to the humeral component. Current RSA systems and techniques can result in the undesirable effects of scapular notching and limited range of motion. Currently practiced solutions to these undesirable effects typically employ a steeper humeral implant angle and, additionally or alternatively, a lateralized center of rotation. Biomechanically derived loading for the humeral component can be estimated based on the muscle activation direction, here, the deltoid muscle, with lack of rotator cuff muscle contribution. This estimation can be fully understood by reference to A. Terrier et al., Simulated joint and muscle forces in reversed and anatomic shoulder prostheses. Journal of Bone & Joint Surgery, British Volume, 90(6) 751-756 (08). As shown in FIG. 1, the primary joint reaction force 102 is in the direction of the humeral axis, combining a compressive load vector 103 and a medial shear load vector 104 on the humeral articular surface. Therefore, steeper humeral implant angles can lead to higher shear (or lever-out) forces 104 experienced by the liner, challenging the liner/tray locking mechanism. Further, lateralization of the center of rotation increases the joint reaction forces necessary to move the arm, which can also challenge the locking mechanism. The instant systems, liners, trays, and associated methods seek to reduce or eliminate these adverse effects by disposing the most robust portion of the locking mechanism laterally to resist the primary load direction. The inventors have found through physical and empirical testing that the asymmetrical locking mechanism can maintain approximately 60% higher shear loading than a conventional circumferential lock mechanism.

Figure 2:
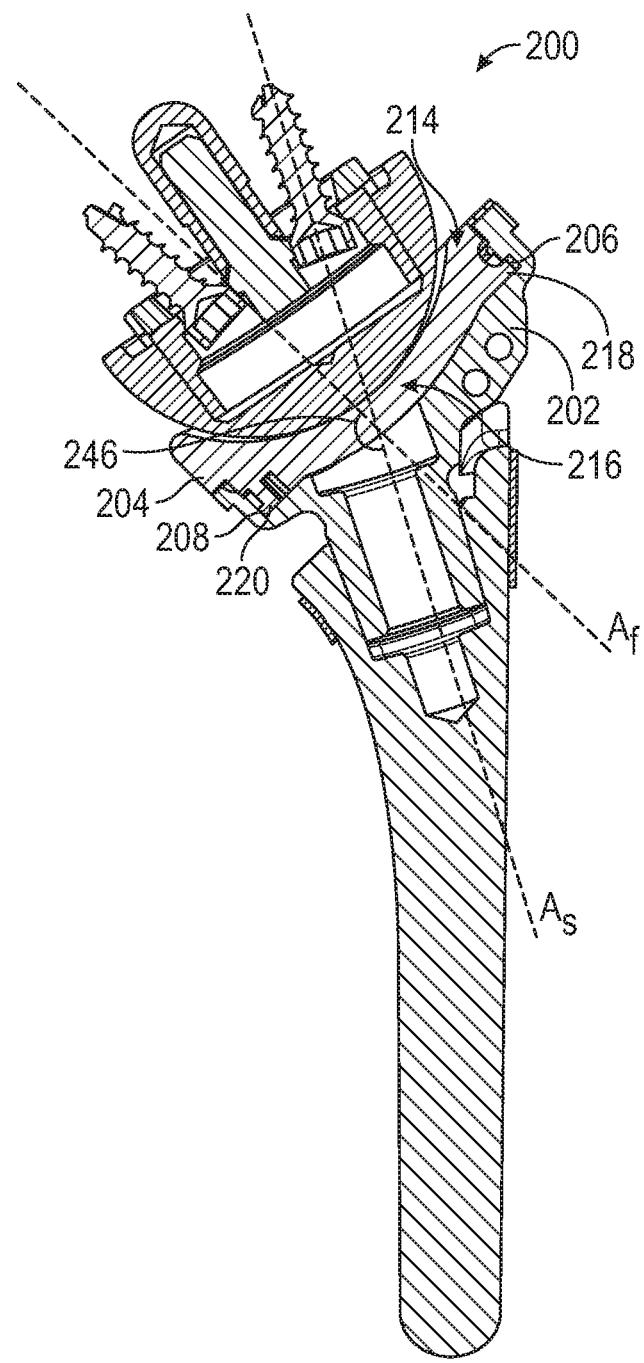
FIG. 2 illustrates a cross-sectional side view of an exemplary prosthesis system according to the present disclosure.
Figure 3:
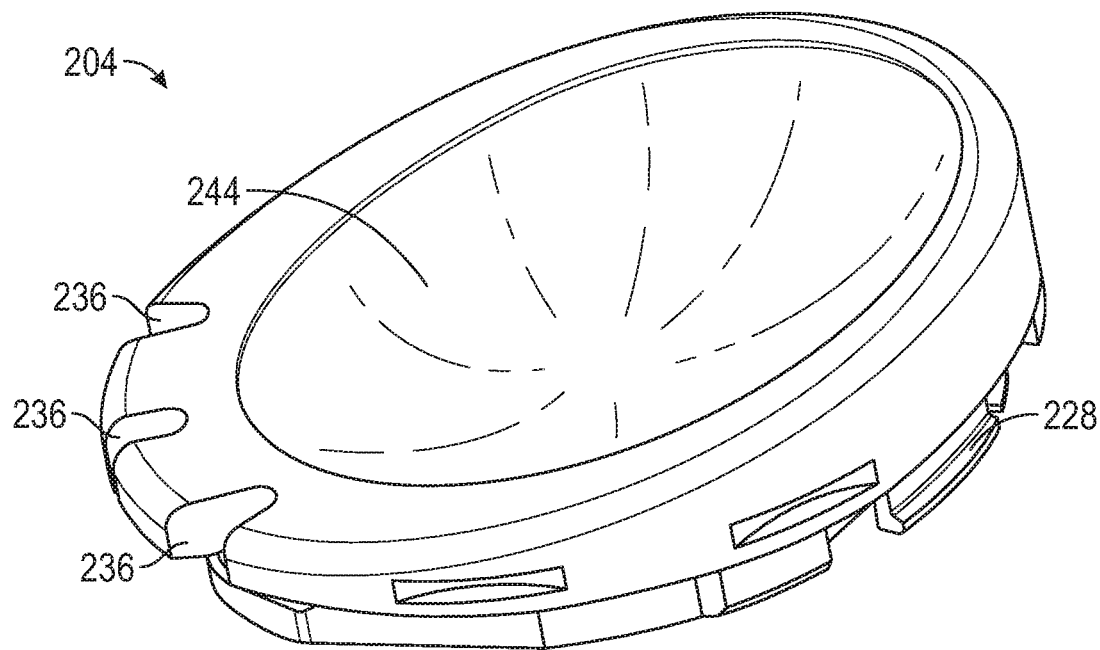
FIG. 3 illustrates a top perspective view of an exemplary liner according to the present disclosure.
Figure 4:
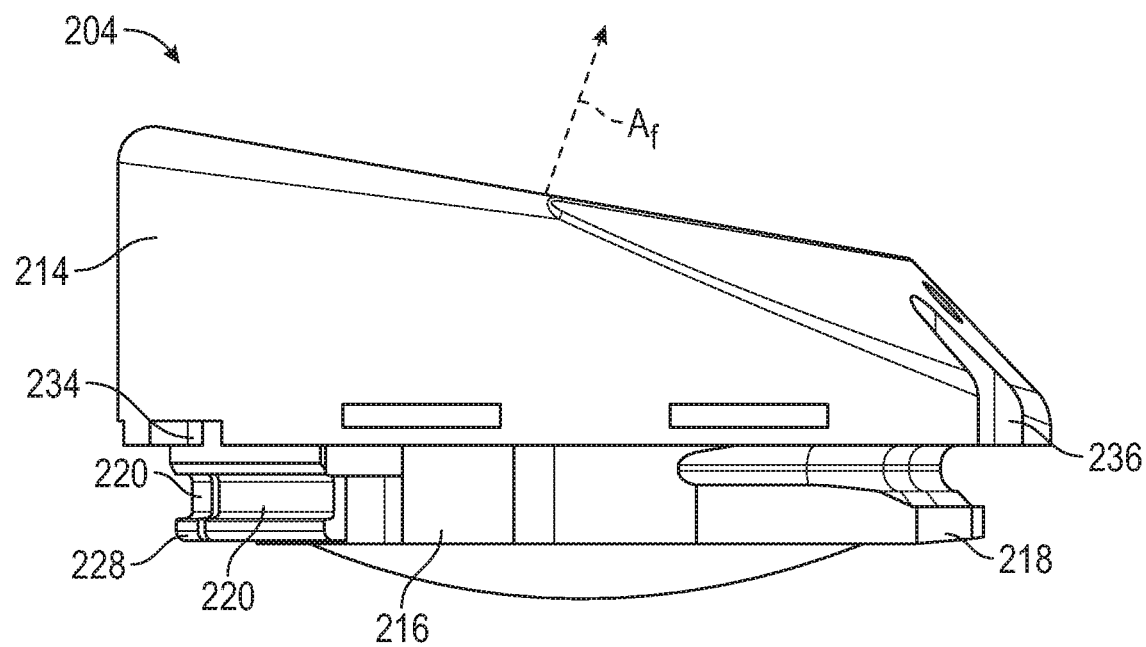
FIG. 4 illustrates a side view of the liner of FIG. 3.
Figure 5:
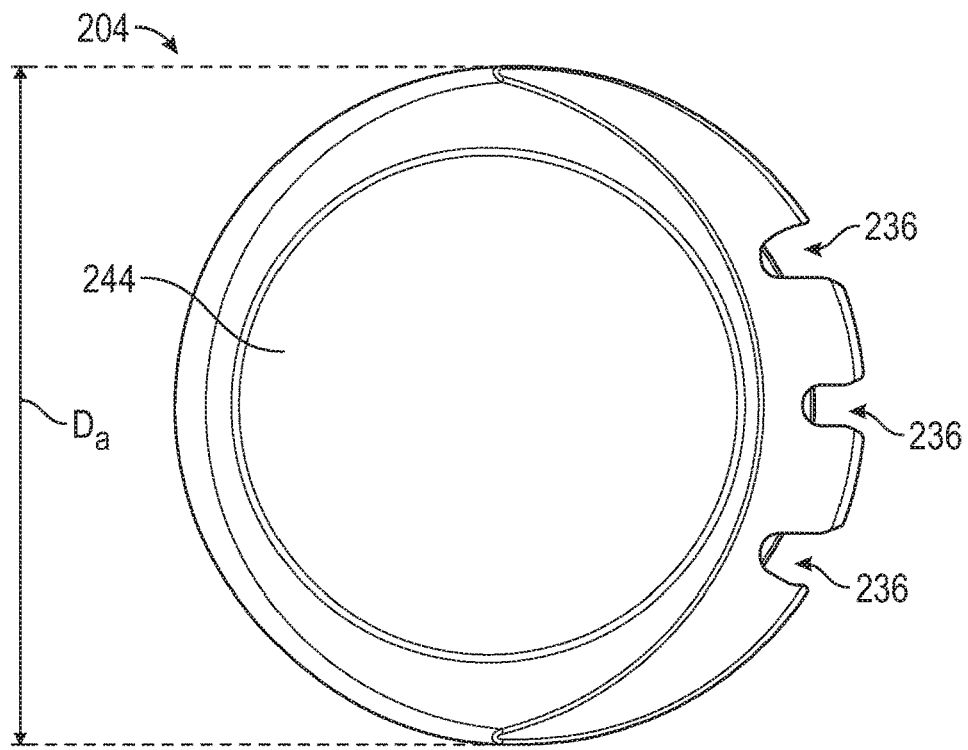
FIG. 5 illustrates a top view of the liner of FIG. 3.
Figure 6:
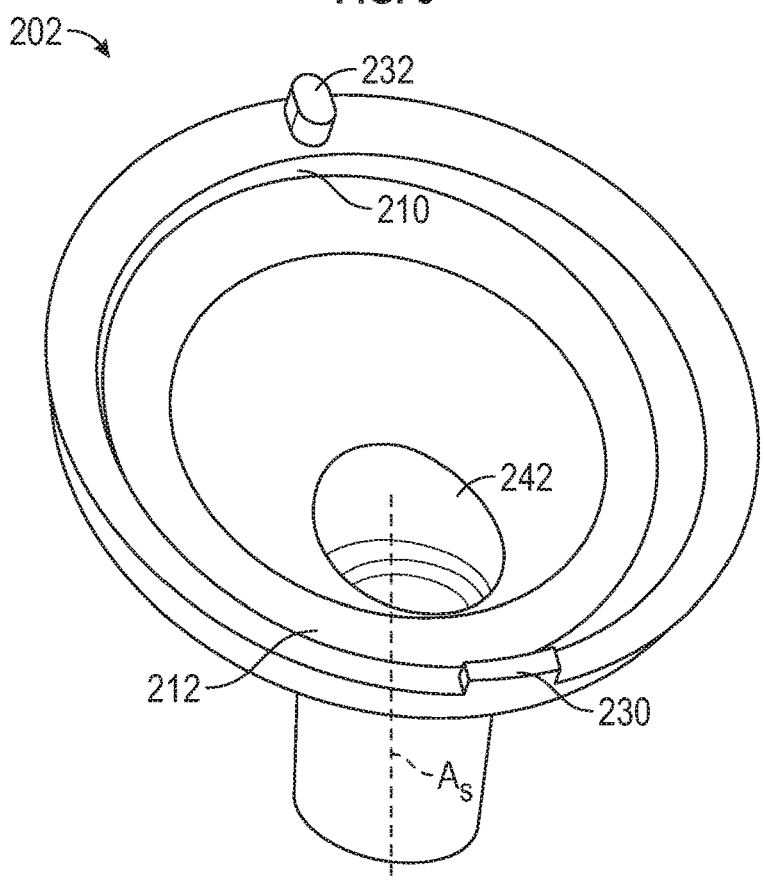
FIG. 6 illustrates a top perspective view of an exemplary tray according to the present invention.

With reference to FIGS. 2-8, a prosthesis system 200 for a joint can comprise a tray 202 and a liner 204. As illustrated in FIG. 2, the tray 202 can have a lateral groove 206 disposed in an inner surface of a lateral circumferential portion 210 of a circumferential lip of the tray 202. The tray 202 can also have a medial groove 208 disposed in an inner surface of a medial circumferential portion 212 of the circumferential lip of the tray 202. The lateral groove 206 and the medial groove 208 can comprise different portions of a single groove extending the circumference of the inner surface of the tray 202. The liner 204 can have an upper segment 214 and a lower segment 216. At least the lower segment 216 can comprise a locking portion for lockingly engaging the tray 202. The locking portion can comprise a lateral toe 218 positioned generally diametrically opposite a plurality of resiliently deformable medial fingers 220 defined therein. The liner 204 and the tray 202 can be engageable in a lateral-to-medial direction so that the plurality of medial fingers 220 can resiliently deform to engage the medial groove 208 subsequent to engagement of the lateral toe 218 within the lateral groove 206. The plurality of medial fingers 220 can comprise from about 2 to about 6 medial fingers. The lateral toe 218 of the liner 204 can remain substantially undeformed during and subsequent to engagement within the lateral groove 206. Upon implantation, the tray 202 and the liner 204 can be selectively rotationally oriented with respect to each other such that the lateral toe 218 of the liner 204 can be engaged within a middle portion of the lateral groove 206 of the tray 202 to resist disassociation of the liner 204 from the tray 202 when the prosthesis is subjected to physiological loading conditions.

In one aspect, the lateral groove 206 of the tray 202 can further comprise a lateral locking lip 222 projecting radially inward from the inner surface of the lateral circumferential portion 210. The lateral toe 218 and the lateral locking lip 222 can cooperate to at least partially secure the liner 204 within the tray 202. In a further aspect, the lateral toe 218 and the lateral locking lip 222 can cooperate to serve as the primary locking feature of the locking mechanism.

In another aspect, the superior surface of the medial groove 208 of the tray 202 is formed by a medial locking lip 224 projecting radially inward from the inner surface of the medial circumferential portion 212 of the tray 202. A medial lead-in ramp 226 can extend from a point above the top surface of the medial locking lip 224 to the top surface of the medial locking lip 224. The medial lead-in ramp 226 provides a surface to guide the one or more resiliently deformable medial fingers 220 over the medial locking lip 224. In another aspect, the plurality of medial fingers 220 can further comprise a snap lip 228 projecting outward from the distal end of each of the plurality of medial fingers 220. The medial fingers 220 can resiliently deform when passing over the medial lead-in ramp 226 and return to a neutral position, for example, once the snap lips 228 pass the medial locking lip 224. The locking lip of the medial groove 208 and the snap lip 228 of each of the plurality of medial fingers 220 cooperate to at least partially secure the liner 204 within the tray 202. In a further aspect, the plurality of medial fingers 220 and the snap lip 228 can serve as a secondary locking feature of the locking mechanism.

In one aspect, the medial circumferential portion 212 of the tray 202 can further comprise a medial tab 230 that can extend from an upper surface thereof. A lower surface of the upper segment 214 of the liner 204 can define a medial female receptacle 234 for matingly receiving the medial tab 230 of the tray 202 in order to prevent rotation of the liner 204 relative to the tray 202 when engaged. The lower surface of the upper segment 214 of the liner 204 can further define a plurality of medial female receptacles 234 for receiving the medial tab 230. The liner 204 can have at least three medial female receptacles 234. Each of the plurality of female receptacles can correspond to a unique angular rotational position between the liner 204 and the tray 202. Each of the plurality of medial female receptacles 234 can have a center-to-center angular rotational measurement of from about 10 degrees to about 60 degrees. In one example, each of the plurality of medial female receptacles 234 can have a center-to-center angular rotational measurement of about 30 degrees. Adjusting the angular rotational position between the liner 204 and the tray 202 can provide for either or both of customizable balancing and customized constraint of the joint that can, for example, enable a surgeon to maximize joint stability.

In another aspect, the lateral circumferential portion 210 of the tray 202 can further comprise a lateral tab 232 that can extend from an upper surface thereof. At least a portion of the upper segment 214 of the liner 204 proximate the lateral toe 218 can define a lateral female receptacle 236 for matingly receiving the lateral tab 232 of the tray 202 in order to prevent rotation of the liner 204 relative to the tray 202 when engaged. At least a portion of the upper segment 214 of the liner 204 proximate the lateral toe 218 can further define a plurality of lateral female receptacles 236, wherein each of the plurality of female receptacles corresponds to a unique angular rotational position between the liner 204 and the tray 202. The liner 204 can have at least three lateral female receptacles 236. Each of the plurality of lateral female receptacles 236 can have a center-to-center angular rotational measurement of from about 10 degrees to about 60 degrees. In one example, each of the plurality of lateral female receptacles 236 can have a center-to-center angular rotational measurement of about 30 degrees.

In another aspect, the tray 202 can have an outside diameter of from about 30 mm to about 50 mm. In one example, the tray 202 can have an outside diameter of about 40 mm.

In one aspect, the tray 202 can have a central through-hole 242 disposed therein. The center through-hole 242 can facilitate, for example, conversion assembly and tray removal. In one example, a tool can be inserted or threaded into the through-hole to lift the tray out of the stem.

In another aspect, an upper segment 214 of the liner 204 can define a face 244 that comprises an articulating surface. The face 244 can have a diameter $D_a$ of from about 30 mm to about 50 mm. In one example, the face 244 can have a diameter of from about 35 mm to about 50 mm. Some exemplary face diameters can include 36 mm, 40 mm, and 42 mm. In another aspect, the face can have a face angle 246 measured between a stem axis $A_s$ and an axis $A_f$ normal to the face of less than about 150 degrees. In another aspect, the face can have a face angle 246 of from about 135 degrees to about 155 degrees.

In one aspect, the liner 204 can comprise polyethylene. The polyethylene can comprise ultra high molecular weight polyethylene. The liner 204 can further comprise vitamin E. In additional or alternative aspects, the liner 204 can be monolithic such that the upper segment 214 and the lower segment 216 are continuous or the upper segment 214 and the lower segment 216 can be joined to form the liner 204.

Figure 7A:
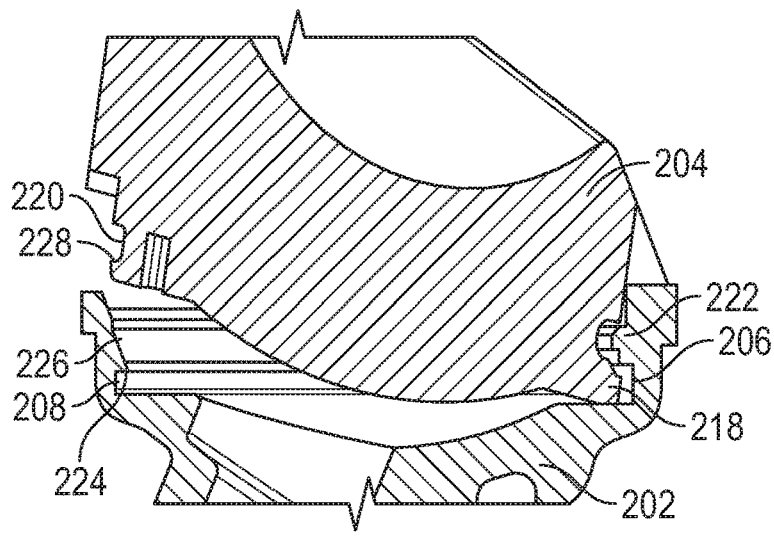
FIGS. 7A-7D illustrate cross-sectional views of an exemplary prosthesis system during the lateral-to-medial engagement of the liner and the tray.
Figure 7B:
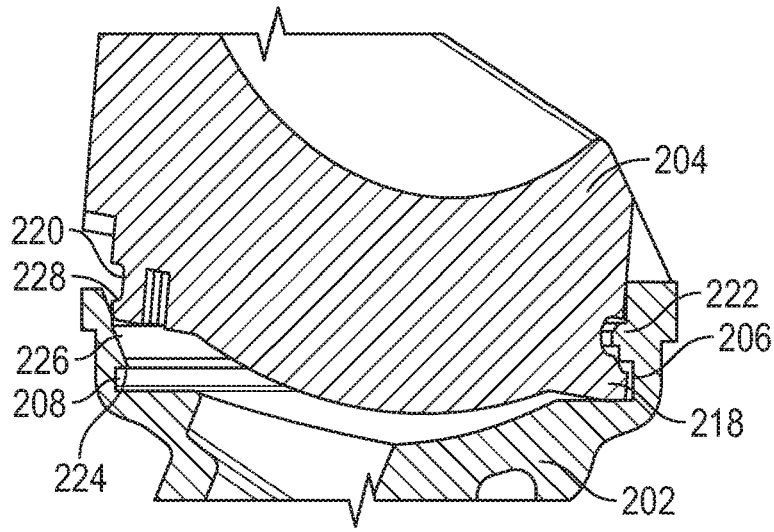
Figure 7C:
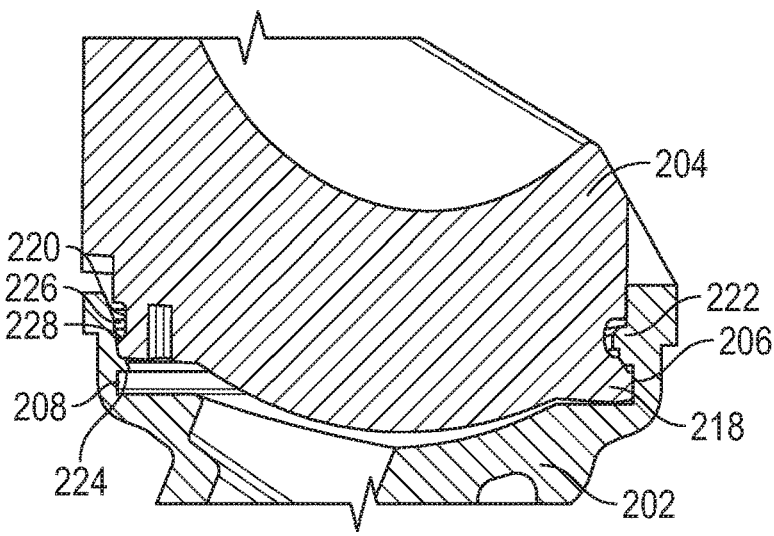
Figure 7D:
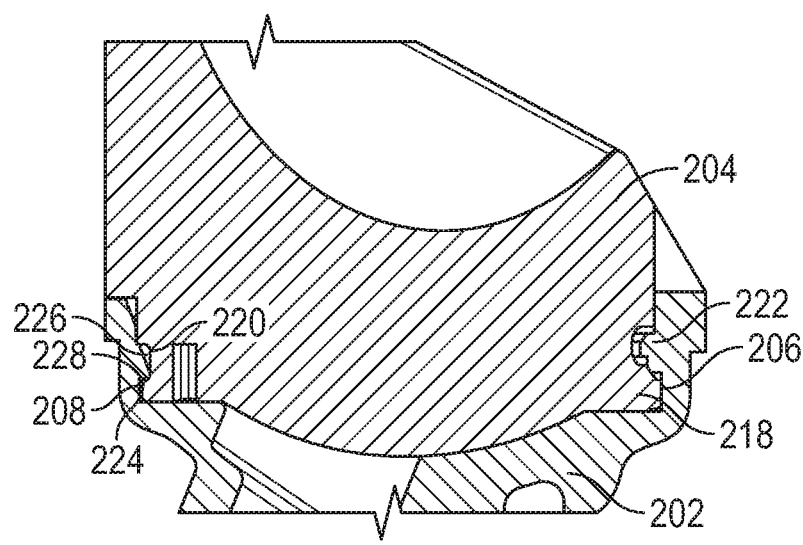
Figure 8:
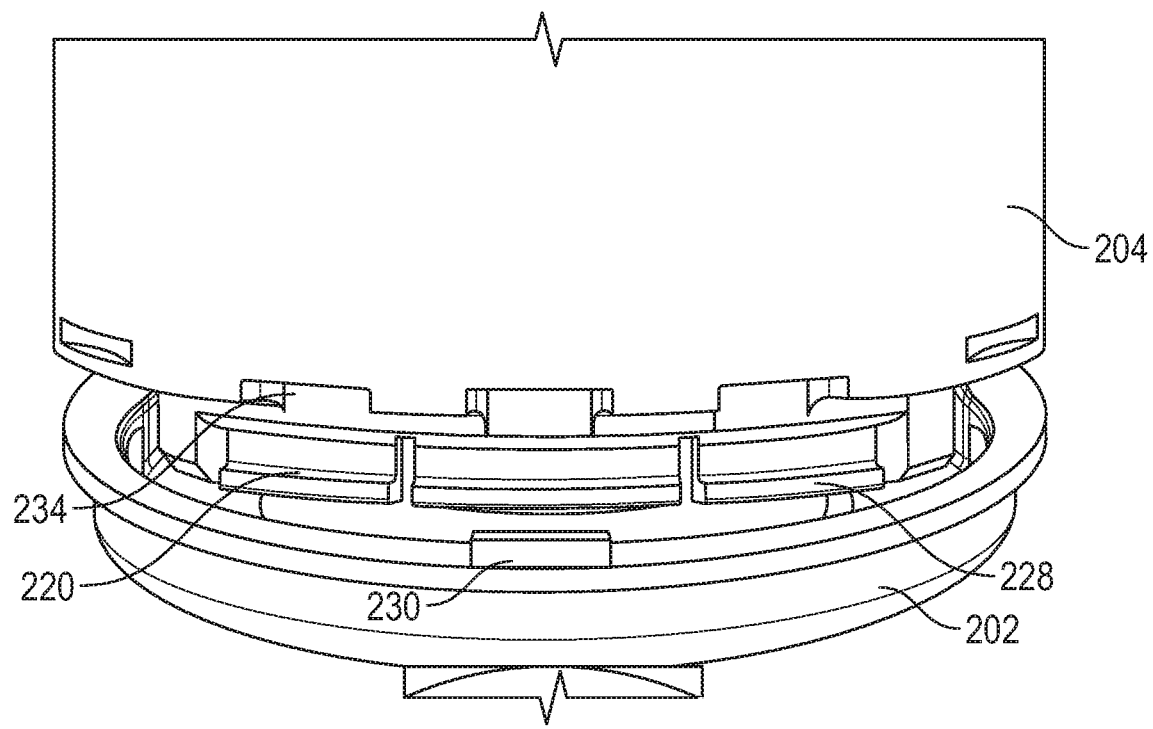
FIG. 8 illustrates a front view of an exemplary prosthesis system during engagement of the liner and the tray.

FIGS. 7A-7D illustrate an exemplary method of assembling the liner 204 into the tray 202. A tray 202 and a liner 204 can be selectively rotationally oriented with respect to each other such that a lateral toe 218 of a lower segment 216 of a liner 204 can be aligned with a middle portion of a lateral groove 206 disposed in an inner surface of a lateral circumferential portion 210 of the tray 202. As shown in FIG. 7A, the lateral toe 218 of the liner 204 can be engaged in the lateral groove 206 of the tray 202 while the lateral tab 232 of the tray 202 can be disposed in a selected one of the plurality of lateral female receptacles 236 of the liner 204. As shown in FIGS. 7B and 7C, a plurality of resiliently deformable medial fingers 220 can be deformed as they are urged into contact with the medial lead-in ramp 226 while the medial tab 232 can be disposed in a selected one of the plurality of medial female receptacles 234. As shown in FIG. 7D, the medial fingers 220 can return to a neutral position, for example, once the snap lips 228 pass the medial locking lip 224. The medial fingers 220 are disposed generally diametrically opposite the lateral toe 218 and the lateral toe 218 resists disassociation of the liner 204 from the tray 202 when the prosthesis is subjected to physiological loading conditions.

Experimental Results

In another aspect, evaluation of resistance to liner dissociation in an exemplary directional locking mechanism according to the present disclosure compared to a conventional circumferential locking mechanism using physical testing and Finite Element Analysis (FEA) was performed. Similar size ultrahigh molecular weight polyethylene (UHMWPE) liners, one with a conventional circumferential locking mechanism design and one with a directional locking mechanism, were assembled per surgical technique in a tray fixture and mounted horizontally in a DI water bath at 37 degrees C. in a testing assembly. A 40 mm load head was used to apply a constant compressive load of 500 N and the load head was translated medially with respect to the fixed liner at a constant rate of 50 mm/min until the liner dissociated from the spacer or tray. Horizontal displacement and shear load values were collected at 100 Hz. A t-test assuming equal variance, with the null hypothesis that there was no difference in peak shear load per design, was used to determine difference in shear load between the circumferential locking design and direction design. A p value of less than 0.05 indicates a significant result. FEA was performed with identical constraints as the physical test setup using Ansys Workbench version 15 (Ansys Inc., Canonsburg, Pa.). Models utilized linear elastic properties for Ti-6Al-4V spacers and trays (modulus: 1.497 GPa poisons ratio: 0.3) and non-linear properties for UHMWPE determined from the literature up to a strain level of 1.64 [5]. Frictional contact between the two metal components and poly component was specified at 0.2. Results were compared to physical testing to validate the FEA model.

Physical testing indicated that the circumferential and directional lock mechanisms resisted peak shear forces of about 511±19 N and about 835±13 N, respectively, a statistically significant difference (p<0.0005). FEA analysis predicted peak shear loads of about 480 N and about 878.6 N, an error of about 6% and about 5% from physical testing results.

Some numbered examples of the present disclosure follow.

Example 1 is a system that can comprise a tray having a circumferential lip forming a recess, the circumferential lip can include a lateral groove disposed in an inner surface of a lateral circumferential portion of the circumferential lip and a medial groove disposed in the inner surface of a medial circumferential portion of the circumferential lip; and a liner coupleable with the tray with a locking portion, wherein the locking portion can comprise a lateral toe configured to engage the lateral groove in the tray and a plurality of medial fingers resiliently deformable to engage the medial groove of the tray to lock the liner onto the tray.

In Example 2, the subject matter of Example 1 optionally includes wherein the liner can define a plurality of medial female receptacles for receiving the medial tab.

In Example 3, the subject matter of Example 2 optionally includes wherein each of the plurality of medial female receptacles can correspond to a unique angular rotational position between the liner and the tray.

In Example 4, the subject matter of any one or more of Examples 2-3 optionally include wherein each of the plurality of medial female receptacles can have a center to center angular rotational measurement of from about 10 degrees to about 60 degrees with respect to adjacent female receptacles.

In Example 5, the subject matter of any one or more of Examples 1-4 optionally include wherein the lateral circumferential portion of the tray can further comprise a lateral tab extending from an upper surface thereof, and wherein the liner proximate the lateral toe can define a lateral female receptacle for matingly receiving the lateral tab of the tray.

In Example 6, the subject matter of Example 5 optionally includes wherein the liner proximate the lateral toe can define a plurality of lateral female receptacles, wherein each of the plurality of female receptacles can correspond to a unique angular rotational position between the liner and the tray.

In Example 7, the subject matter of any one or more of Examples 1-6 optionally include wherein a superior surface of the medial groove can be formed by a medial locking lip projecting radially inward from the inner surface of the medial circumferential portion of the tray.

In Example 8, the subject matter of Example 7 optionally includes a medial lead-in ramp that can extend from a point above a top surface of the medial locking lip to the top surface of the medial locking lip.

In Example 9, the subject matter of any one or more of Examples 1-8 optionally include wherein the tray can have a central through-hole disposed therein.

In Example 10, the subject matter of any one or more of Examples 1-9 optionally include wherein each of the plurality of medial fingers can further comprise a snap lip projecting radially outward from a distal end thereof.

In Example 11, the subject matter of any one or more of Examples 1-10 optionally include wherein the upper segment of the liner can define a face comprising articulating surface.

In Example 12, the subject matter of Example 11 optionally includes wherein the articulating surface can have a diameter of from about 35 mm to about 55 mm.

In Example 13, the subject matter of any one or more of Examples 1-12 optionally includes wherein the face can have a face angle of less than about 150 degrees as measured between a stem axis and an axis normal to the face.

In Example 14, the subject matter of any one or more of Examples 1-13 optionally include wherein the face can have a face angle of from about 135 degrees to about 155 degrees.

Example 15 is a method that can comprise selectively rotationally orienting a tray and a liner with respect to each other such that a lateral toe of a liner is aligned with a middle portion of a lateral groove disposed in an inner surface of a lateral circumferential portion of a circumferential lip of the tray; engaging the lateral toe of the liner in the lateral groove of the tray; and engaging a plurality of resiliently deformable medial fingers defined in the lower segment of the liner within a medial groove disposed in an inner surface of a medial circumferential portion of the circumferential lip, wherein the medial fingers are disposed generally diametrically opposite the lateral toe; wherein the lateral toe and the lateral groove cooperate to resist disassociation of the liner from the tray when the prosthesis is subjected to physiological loading conditions in use.

In Example 16, the subject matter of Example 15 optionally includes engaging a medial tab extending from an upper surface of the medial circumferential portion of the circumferential lip with a medial female receptacle defined in the upper segment of the liner.

In Example 17, the subject matter of Example 16 optionally includes engaging the medial tabs extending from an upper surface of the medial circumferential portion of the circumferential lip with a selected one of a plurality of uniquely angularly oriented medial female receptacle defined in the upper segment of the liner.

In Example 18, the subject matter of any one or more of Examples 15-17 optionally includes engaging a lateral tab extending from an upper surface of the lateral circumferential portion of the circumferential lip with a lateral female receptacle defined in at least a portion of the upper segment of the liner.

In Example 19, the subject matter of Example 18 optionally includes engaging the lateral tab extending from an upper surface of the lateral circumferential portion of the circumferential lip with a selected one of a plurality of uniquely angularly oriented lateral female receptacles defined in the upper segment of the liner.

In Example 20, the subject matter of Example 18 optionally includes engaging the lateral tab extending from an upper surface of the lateral circumferential portion of the circumferential lip with a selected one of a plurality of uniquely angularly oriented lateral female receptacles defined in the upper segment of the liner.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled. As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A prosthesis system for a joint, comprising:
   a tray having a circumferential lip forming a recess, the circumferential lip including a lateral groove disposed in an inner surface of a lateral circumferential portion of the circumferential lip and a medial groove disposed in an inner surface of a medial circumferential portion of the circumferential lip, the medial circumferential portion further including a medial tab extending from an upper surface thereof and defining a first shape, and the lateral circumferential portion further including a lateral tab extending from an upper surface thereof and defining a second shape different than the first shape; and a liner coupleable with the tray with an asymmetrical locking portion, the asymmetrical locking portion comprising a lateral toe configured to engage the lateral groove in the tray and a plurality of medial fingers that are resiliently deformable to engage the medial groove of the tray to lock the liner onto the tray, the lateral toe positioned generally diametrically opposite the plurality of medial fingers, the liner defining at least three medial female receptacles, each of the medial female receptacles formed as a recess in an outer edge of the liner having the first shape such that each of the medial female receptacles is mateable with the medial tab of the tray, and the liner proximate the lateral toe defining at least three lateral female receptacles, each of the lateral female receptacles formed as a recess in an opposing outer edge of the liner having the second shape such that each of the lateral female receptacles is mateable with the lateral tab of the tray;

wherein each of the medial female receptacles corresponds to a unique angular rotational position between the liner and the tray;

wherein the liner and the tray are engageable in a lateral-to-medial direction so that the plurality of medial fingers resiliently deform to engage the medial groove subsequent to engagement of the lateral toe within the lateral groove; and wherein the lateral toe remains substantially undeformed during and subsequent to engagement within the lateral groove.

2. The prosthesis system of claim 1, wherein each of the medial female receptacles corresponds to an angular rotational position between the liner and the tray of from about 10 to about 60 degrees with respect to the angular rotation position between the liner and the tray corresponding to adjacent female receptacles.

3. The prosthesis system of claim 1, wherein a superior surface of the medial groove is formed by a medial locking lip projecting radially inward from the inner surface of the medial circumferential portion of the tray.

4. The prosthesis system of claim 3, further comprising a medial lead-in ramp extending from a point above a top surface of the medial locking lip to the top surface of the medial locking lip.

5. The prosthesis system of claim 1, wherein the tray has a central through-hole disposed therein.

6. The prosthesis system of claim 1, wherein each of the plurality of medial fingers further comprises a snap lip projecting radially outward from a distal end thereof.

7. The prosthesis system of claim 1, wherein an upper segment of the liner defines a face comprising an articulating surface.

8. The prosthesis system of claim 7, wherein the articulating surface has a diameter of from about 35 mm to about 55 mm.

9. The prosthesis system of claim 7, wherein the face has a face angle of less than about 150 degrees as measured between a stem axis and an axis normal to the face.

10. The prosthesis system of claim 7, wherein the face has a face angle of from about 135 degrees to about 155 degrees as measured between a stem axis and an axis normal to the face.

11. The prosthesis system of claim 1, wherein the lateral toe and the lateral groove cooperate to resist a primary shear load applied to the liner under physiological loading conditions.

12. The prosthesis system of claim 1, wherein the liner comprises a lower segment including the plurality of medial fingers and the lateral toe and an upper segment defining an articulating surface, wherein a medial height of the liner defined between the lower segment and the upper segment is greater than a lateral height of the liner defined between the lower segment and the upper segment, and wherein the articulating surface is spaced closer to a medial circumferential edge of the upper segment of the liner than a lateral circumferential edge of the upper segment of the liner.

* * * * *